United States Patent
Guo et al.

(10) Patent No.: US 10,414,795 B2
(45) Date of Patent: Sep. 17, 2019

(54) TECHNIQUES OF PREPARING COLLAGEN ACTIVE PEPTIDES

(71) Applicants: Technical Institute of Physics and Chemistry, Chinese Academy of Sciences, Beijing (CN); Baotou Dongbao Bio Tech Co Ltd., Baotou (CN); Eric Hanxiang Sun, Culver City, CA (US)

(72) Inventors: Yanchuan Guo, Beijing (CN); Bing Zhang, Beijing (CN); Fang Liu, Baotou (CN); Furong Wang, Baotou (CN); Eric Hanxiang Sun, Culver City, CA (US); Jianing Wang, Beijing (CN)

(73) Assignees: TECHNICAL INSTITUTE OF PHYSICS AND CHEMISTRY, CHINESE ACADEMY OF SCIENCES, Beijing (CN); BAOTOU DONGBAO BIO TECH CO LTD., Baotou (CN); Eric Hanxiang Sun, Culver City, CA (US)

( * ) Notice: Subject to any disclaimer, the term of this patent is extended or adjusted under 35 U.S.C. 154(b) by 213 days.

(21) Appl. No.: 15/459,437

(22) Filed: Mar. 15, 2017

(65) Prior Publication Data
US 2017/0267746 A1    Sep. 21, 2017

(30) Foreign Application Priority Data
Mar. 16, 2016    (CN) .......................... 2016 1 0149640

(51) Int. Cl.
| C07K 1/36 | (2006.01) |
| C07K 14/78 | (2006.01) |
| C12P 21/06 | (2006.01) |
| C07K 1/18 | (2006.01) |
| C07K 1/34 | (2006.01) |

(52) U.S. Cl.
CPC .................. *C07K 1/36* (2013.01); *C07K 1/18* (2013.01); *C07K 1/34* (2013.01); *C07K 14/78* (2013.01); *C12P 21/06* (2013.01)

(58) Field of Classification Search
CPC .......... C12P 21/00; C12P 21/06; C07K 14/78; C07K 1/36; C07K 1/34; C07K 1/18
See application file for complete search history.

(56) References Cited

U.S. PATENT DOCUMENTS

2006/0269987 A1* 11/2006 Dolphin ................... C08H 1/06
                                                                    435/68.1
2016/0213591 A1*  7/2016 Zhou ..................... A61K 35/36

FOREIGN PATENT DOCUMENTS

WO    WO-2015043115 A1 *  4/2015    ............. A61K 35/36

OTHER PUBLICATIONS

Seabra, IJ et al. Cotton gauze bandage: a support for protease immobilization for use in biomedical applications. Brazilian Journal of Pharmaceutical Sciences. 2007. 43(4): 535-542. (Year: 2007).*
Khiari, Z et al. Low molecular weight bioactive peptides derived from the enzymatic hydrolysis of collagen after isoelectric solubilization/precipitation process of turkey by-products. Poultry Science. 2014. 93(9): 2347-2362. (Year: 2014).*

* cited by examiner

*Primary Examiner* — Renee Claytor
*Assistant Examiner* — Susan E. Fernandez
(74) *Attorney, Agent, or Firm* — Locke Lord LLP; Tim Tingkang Xia, Esq.

(57) ABSTRACT

A method of preparing collagen active peptides with antiproliferative activity against cancer cells. The collagen active peptides are obtained by hydrolysis of papain and trypsin and a specific purifying process. The collagen active peptides have antiproliferative activity against cancer cells, such as ovarian carcinoma cells including SKOV3, OVCAR3, 436 and SRO82 and the prostate cancer cells including PC3, LnCAPC1, and LnCAPC2.

19 Claims, 3 Drawing Sheets

TECHNIQUES OF PREPARING COLLAGEN ACTIVE PEPTIDES

CROSS-REFERENCE TO RELATED APPLICATIONS

This non-provisional application claims priority to and benefit of, under 35 U.S.C. § 119(a), Patent Application No. 201610149640.8 filed in P.R. China on Mar. 16, 2016, the entire content of which is hereby incorporated by reference.

FIELD

The present disclosure relates generally to a method of preparing proteins and polypeptides, and more particularly to a method of preparing active peptides from collagen.

BACKGROUND

Cancer is one of the leading causes of death. In human body tissues, cell differentiation is a physiological process, and in a normal physiological environment, proliferation and death of cells maintain a sort of balance. External environment such as radiation and air pollution may cause mutations of deoxyribonucleic acid (DNA) of a human body, thus breaking a normal regulating process of the human body and causing cancer. On either the cell level or the gene level, cells in cancer genesis are uncontrollably differentiated, form a malignant tumor, and diffuses to other parts of the human body. The American Cancer Society estimated that 21,290 new cases of ovarian cancer would be diagnosed in the United States during 2015. Approximately 14,180 deaths were expected to be caused by ovarian cancer in the United States in 2015. Ovarian cancer is the fifth leading cause of cancer-related death among woman, which exceeds other female reproductive system diseases. A woman's lifetime risk of developing invasive ovarian cancer is 1 in 75, and a woman's lifetime risk of dying from invasive ovarian cancer is about 1 in 100 (the statistic data does not contain low malignant ovarian tumors).

There is a need to utilize biologically active peptides having varied active effects and inhibiting activities to treat tumor cells.

SUMMARY

In one aspect, the present disclosure provides collagen active peptides with antiproliferative activity against cancer cells.

In one embodiment, a method for preparing active peptides from collagen with a antiproliferative activity against cancer cells includes the following steps:

(1) mixing gelatin with water to form a 10-25% gelatin solution;

(2) heating the gelatin solution to 40-75° C., adjusting the pH to 5.0-6.5, and adding papain to perform enzymolysis to obtain a first enzymolysis reaction solution;

(3) adjusting temperature of the first enzymolysis reaction solution to 40-75° C., adjusting the pH to pH7.0-8.5, and adding trypsin to obtain a second enzymolysis reaction solution;

(4) adjusting the pH of the second enzymolysis reaction solution to pH5.5-6.5;

(5) deactivating the protease in the second enzymolysis reaction solution, and then cooling the second enzymolysis reaction solution to be below 40° C. to obtain a crude product solution;

(6) filtering the crude product solution to obtain filtered crude product solution;

(7) filtering the filtered crude product solution using an ultrafiltration membrane having a molecular weight cutoff of 1500 Da to obtain a first filtrate;

(8) filtering the first filtrate using an ultrafiltration membrane having a molecular weight cutoff of 300 Da to obtain a concentrated solution, and lyophilizing the concentrated solution to obtain lyophilized product;

(9) purifying the lyophilized product obtained in step (8) using a cation exchange column to obtain a purified product;

(10) desalting the purified product obtained in step (9) to obtain collagen active peptides solution; and (11) lyophilizing the collagen active peptides solution obtained in step (10) to obtain powdery collagen active peptides.

In certain embodiments, the enzyme dosage of papain in step (2) is 1%-2% of the dry mass of gelatin, and the total enzymolysis reaction time is 30 minutes (min)-4 hours (h).

In certain embodiments, the enzyme dosage of trypsin in step (3) is 1%-2% of the dry mass of gelatin, and enzymolysis reaction time is 30 min-4 h.

In certain embodiments, the enzymolysis temperature of trypsin is 50-55° C.

The gelatin mainly comes from collagen and the collagen is extracellular fibrous protein. Through the enzymolysis reaction by the papain and trypsin, gelatin molecules are degraded into polypeptides with different molecular weights, namely collagen peptides. The gelatin is selected from one or more of bovine bone gelatin, porcine bone gelatin and fish skin gelatin.

In certain embodiments, the protease deactivating method is heating deactivating. In one embodiment, the heating temperature is 95-100° C., and in one embodiment, the protease is deactivated at 95-100° C. for 15 min.

In certain embodiments, the second enzymolysis reaction solution is cooled by a cooling circulating system. In certain embodiments, the second enzymolysis reaction solution is cooled to be below 40° C. within 30 minutes to avoid further degrading of peptide fragments in the second enzymolysis reaction solution. In certain embodiments, the pH value of the first enzymolysis solution in step (3) is adjusted using sodium hydroxide, sodium bicarbonate, or potassium citrate. In one embodiment, the pH value of the first enzymolysis solution in step (3) is adjusted using food grade sodium hydroxide.

In certain embodiments, the pH value of the second enzymolysis solution in step (4) is adjusted using citric acid, acetic acid, or phosphoric acid. In one embodiment, the pH value of the second enzymolysis solution in step (4) is adjusted using food grade citric acid.

In certain embodiments, the pH value of the gelatin solution in step (2) is adjusted using sodium bicarbonate, phosphoric acid, or citric acid.

In certain embodiments, the crude product solution is filtered by a cotton cake filter to remove naked-eye visible impurities in the solution.

In certain embodiments, the crude product solution is further filtered using the ultrafiltration membrane having a molecular weight cutoff of 1500 Da to obtain collagen active peptides capable of penetrating through the filtering membrane and having a molecular weight being smaller than 1500 Da. In order to improve the yield of the collagen active peptides, the concentration of the collagen active peptides in the crude product solution is maintained at 5+/−0.5% (mass volume concentration). After concentrating by the ultrafiltration membrane, water, preferably deionized water, is added into the crude product solution to control the collagen active peptides concentration in the crude product solution to be at 5+/−0.5%. When the concentration of the collagen active peptides having the molecular weight being smaller than 1500 Da in the filtrate is below 0.1% (mass volume concentration), the filtering is stopped.

The first filtrate obtained above is further concentrated using the ultrafiltration membrane having a molecular weight cutoff of 300 Da to obtain a concentrated solution and a second filtrate. The aim of concentrating the collagen active peptides is achieved by filtering out the water molecules, and the collagen active peptides being lower than 300 Da can be further removed. Finally, the collagen active peptides having the molecular weight being lower than 1500 Da and higher than 300 Da are kept in the concentrated solution. In certain embodiments, when the concentration of the collagen active peptides having the molecular weight being lower than 300 Da in the second filtrate is lower than 0.1%, the concentrating process is stopped, when the concentration of the collagen active peptides in the concentrated solution is larger than 10% and the concentration of the collagen active peptides having the molecular weight being lower than 300 Da in the second filtrate is still above 0.1%, the concentrated solution is diluted by adding water till the concentration of the collagen active peptides having the molecular weight being lower than 300 Da in the filtrate is lower than 0.1%, and the concentrated solution is then collected. The collagen active peptides having the molecular weight of lower than 300 Da are removed as much as possible. In one embodiment, a nanofiltration membrane having a molecular weight cutoff of 300 Da of GE Company is used for concentrating.

Components of a penetration peak are collected in the purification of step (9). That is, the components do not bind with the cation column are collected. The purification by the cation column is to remove the collagen active peptides that are capable of binding to the cation column medium.

Through determination by an MTT method, the collagen active peptides have activity of inhibiting proliferation of cancer cells. The cancer cells include ovarian carcinoma cells and prostate cancer cells. The ovarian carcinoma cells include SKOV3, OVCAR3, 436 and SRO82, and the prostate cancer cells includes PC3, LnCAPC1, and LnCAPC2.

In one aspect, the present disclosure relates to a method of preparing collagen active peptides with antiproliferative activity against cancer cells. In certain embodiments, the method includes: performing proteolysis of gelatin using a first protease to obtain a first solution; performing proteolysis of the first solution using a second protease to obtain a second solution; and purifying collagen active peptides from the second solution.

In certain embodiments, the gelatin is selected from one or more of bovine bone gelatin, pig bone gelatin and fish skin gelatin.

In certain embodiments, the first protease is papain, and the step of performing proteolysis of gelatin using the first protease to obtain the first solution comprises: mixing the gelatin with water to form a 10-25% gelatin solution; and heating the gelatin solution to 40-75° C., adjusting a pH of the gelatin solution to pH5.0-6.5, and adding the papain for enzymolysis to obtain the first solution. In certain embodiments, an enzyme dosage of the papain is 1%-2% of a dry mass of the gelatin, and a enzymolysis reaction time by the papain is in a range of about 30 minutes to about 4 hours.

In certain embodiments, the second protease is trypsin, and the step of performing proteolysis of the first solution using the second protease to obtain the second solution comprises: adjusting a temperature of the first solution to 40-75° C., adjusting a pH of the first solution to pH7.0-8.5, and adding trypsin to obtain the second solution. In certain embodiments, an enzyme dosage of the trypsin is 1%-2% of dry mass of the gelatin, and an enzymolysis reaction time by the trypsin is in a range of about 30 minutes to about 4 hours.

In certain embodiments, the method further comprising, after the step of performing proteolysis of the first solution using the second protease to obtain the second solution, and before the step of purifying the collagen active peptides from the second solution: adjusting a pH of the second solution to pH5.5-6.5 to deactivate the papain and the trypsin in the second solution; and cooling the second solution to be below 40° C. to obtain a crude product solution.

In certain embodiments, the step of purifying the collagen active peptides from the second solution comprises: performing a first filtering to the crude product solution using a cotton cake filter to obtained a filtered crude product solution; performing a second filtering to the filtered crude product solution using an ultrafiltration membrane having a molecular weight cutoff of 1500 Da to obtain a first filtrate; performing a third filtering to the first filtrate with an ultrafiltration membrane having a molecular weight cutoff of 300 Da to obtain a concentrated solution, and lyophilizing the concentrated solution to obtain a lyophilized product; performing cation exchange chromatography to the lyophilized product to obtain a purified product; desalting the purified product to obtain a collagen active peptides solution; and lyophilizing the collagen active peptides solution to obtain the collagen active peptide in a form of powder.

In certain embodiments, during the step of the second filtering, a concentration of the collagen active peptides in the crude product solution is maintained at 5+/−0.5%, and when the concentration of the collagen active peptides in the filtrate is below 0.1%, the second filtering is stopped; and during the step of the third filtering, when the concentration of the collagen active peptides having a molecular weight being lower than 300 Da in the second filtrate is lower than 0.1%, the third filtering is stopped.

Certain embodiments of the present disclosure have the following beneficial advantages:

(1) The gelatin is taken as a substrate, which is subjected to enzymolysis reaction using food grade enzymes. The raw materials are safe, and the preparing process is simple, easy for operation, and easy for large-scale production.

(2) The low molecular weight peptide components with antiproliferative activity against cancer cells are effectively collected by ultrafiltration and nanofiltration. The components having the molecular weight less than 1500 Da is above 90%, which is easily absorbable by a human body. A coil filter membrane used in ultrafiltration is easy for realizing batch separation of the enzymatic hydrolysate.

(3) From a cellular level, the collagen active peptides have high antiproliferative activity against cancer cells.

DETAILED DESCRIPTION

In order to clearly describe the present disclosure, the present disclosure is further described in combination with preferable embodiments and accompanying drawings. Similar parts in the accompanying drawings are denoted by same or similar accompanying drawings marks. Those skilled in the art should understand that the specifically described content below is illustrative rather than limitative and should not limit a protective scope of the present disclosure.

Biologically active peptides from food represents a resource that is capable of promoting health of humankind. These active peptides can be absorbed in the gastrointestinal digestion process and generate activity, and further provide new applications to prevent or treat chronic diseases. Certain polypeptides have immune regulating, antimicrobial, anti-hypertension, anti-thrombosis, anticancer, antioxidant, and cholesterol reducing activities. These active polypeptides come from cow milk, wheat, soybean, eggs, fish protein and other plants and animals, and may be prepared through an enzyme hydrolysis method or fermentation method.

Porcine skin gelatin exerted strong antiproliferative activity against K-562, HCT-15 and AGS cells. The growth inhibiting effect of whey protein isolate and collagen hydrolysate on B16F10 melanoma cancer cells and the influence of the whey protein isolate and collagen hydrolysate on cell cycle phases are studied. The results show that the whey protein isolate and collagen hydrolysate have obvious growth inhibiting effect on the B16F10 cells, with the median inhibitory concentration $IC_{50}$ between 0.19-156.9 mg/mL. Further, the median inhibitory concentration $IC_{50}$ of a bovine collagen hydrolysate on the B16F10 cell is lower than 1 mg/mL. A heated pepsin hydrolysate from a marine fish half-fin anchovy has antiproliferative activities on human prostate cancer cell line DU145 with an $IC_{50}$ of 13.67 mg/mL, and has antiproliferative activities on human lung cancer cell line 1299 with a median inhibitory concentration $IC_{50}$ of 25.17 mg/mL. Loach protein hydrolysates prepared by papain digestion has antiproliferative activities against liver cancer cell line HepG2, breast cancer cell line MCF-7, and rectal cancer cell line Caco-2. When the protein concentration was up to 40 mg/mL, the proliferation rates of the HepG2 and MCF-7 were respectively only 7% and 4% of the control group (the group without the polypeptides).

A hydrophobic peptide extracted from anchovy sauce has an inhibiting effect on a human lymphoma cell U937. The amino acids constituting the peptide are alanine and phenylalanine, and the molecular weight of the peptide is 440.9 dalton (Da). Protein hydrolysates from tuna cooking juice has an inhibiting effect on proliferation of human breast cancer cell line MCF-7, and the fraction separated through an ultrafiltration membrane and having a molecular weight larger than 2500 Da, has high antiproliferative activity against the MCF-7, with an $IC_{50}$ of 1.39 mg/mL. After separation and purification using multiple chromatography, two anticancer peptides were obtained. The obtained peptides were sequenced, and the sequences of the peptides are KPEGMDPPLSEPEDRRDGAAGPK (2449.292 Da)
and KLPPLLLAKLLMSGKLLAEPCTGR (2562.405 Da).

Kuo-Chiang Hsu used commercial protein enzymes to hydrolyze tuna dark muscle byproduct, and the produced protein hydrolysates were evaluated for their antiproliferative activities against human breast cancer cell line MCF-7. The protein hydrolysates were filtered by gel filtration and purified by High Performance Liquid Chromatography (HPLC) to obtain two anticancer peptides with amino acid sequences of Leu-Pro-His-Val-Leu-Thr-Pro-Glu-Ala-Gly-Ala-Thr (1206 Da) and Pro-Thr-Ala-Glu-Gly-Val-Tyr-Met-Val-Thr (1124 Da). Both the two peptides show dose-dependent inhibition effect against the MCF-7 cells, with $IC_{50}$ of 8.1 μM and 8.8 μM, respectively. This result indicates that the tuna dark muscle byproduct has potential medicinal value on inhibiting cancer cell proliferation. Aleman studied the antiproliferative activity of squid gelatin hydrolysates on the human breast cancer cell line MCF-7 and brain cancer cell line U87. The $IC_{50}$ are 0.13 and 0.10 mg/mL, respectively. Therefore, biologically active peptides have varied active effects, and their inhibiting activity on tumor cells plays an important role on developing anticancer drugs. In certain embodiments, the present disclosure aims to provide active peptides derived from collagen, which has antiproliferative activity against cancer cells.

In one aspect, the present disclosure relates to a method of preparing collagen active peptides with antiproliferative activity against cancer cells. In certain embodiments, the gelatin is selected from one or more of bovine bone gelatin, pig bone gelatin and fish skin gelatin. In certain embodiments, the method includes: performing proteolysis of gelatin using a first protease to obtain a first solution; performing proteolysis of the first solution using a second protease to obtain a second solution; and purifying collagen active peptides from the second solution. In certain embodiments, the first protease is papain, and the second protease is trypsin. In other embodiments, the first protease is trypsin and the second protease is papain. In further embodiments, each of the first protease and second protease may be selected from serine proteases, cysteine proteases, threonine proteases, aspartic proteases, glutamic proteases, metalloproteases other than the trypsin and the papain.

In certain embodiments, the first protease is papain, and the step of performing proteolysis of gelatin using the first protease to obtain the first solution comprises: mixing the gelatin with water to form a 10-25% gelatin solution; and heating the gelatin solution to 40-75° C., adjusting a pH of the gelatin solution to pH5.0-6.5, and adding the papain for enzymolysis to obtain the first solution. In certain embodiments, an enzyme dosage of the papain is 1%-2% of a dry mass of the gelatin, and an enzymolysis reaction time by the papain is in a range of about 30 minutes to about 4 hours. In certain embodiments, the gelatin in the gelatin solution may be less than 10% or higher than 25%, as long as the enzymolysis is efficient with appropriate amount of papain. In certain embodiments, the gelatin solution is heated to about 60-70° C. for achieve optimal enzymolysis with papain. In one embodiment, the gelatin solution is heated to about 65° C. In certain embodiments, the pH of the gelatin solution is adjusted to about 6.0-7.0 for achieve optimal enzymolysis with papain. In one embodiment, the pH of the gelatin solution is adjusted to about pH6.5. In one embodiment, the pH of the gelatin solution is adjusted to about pH6.5. In certain embodiment, the temperature, the pH and the amount of papain used may be determined according to the user manual recommended by the manufacture of the papain for optimal enzymolysis. In certain embodiment, the temperature, the pH and the amount of papain may be determined in advance for optimal enzymolysis.

In certain embodiments, the second protease is trypsin, and the step of performing proteolysis of the first solution using the second protease to obtain the second solution comprises: adjusting a temperature of the first solution to 40-75° C., adjusting a pH of the first solution to pH7.0-8.5, and adding trypsin to obtain the second solution. In certain embodiments, an enzyme dosage of the trypsin is 1%-2% of dry mass of the gelatin, and a enzymolysis reaction time by the trypsin is in a range of about 30 minutes to about 4 hours. In certain embodiments, the pH of the first solution is adjusted to about 7-9 for achieve optimal enzymolysis with papain. In one embodiment, the pH of the gelatin solution is adjusted to about pH7.6. In certain embodiment, the temperature, the pH and the amount of papain used may be determined according to the user manual recommended by the manufacture of the papain for optimal enzymolysis. In certain embodiment, the temperature, the pH and the amount of papain may be determined in advance for optimal enzymolysis. In certain embodiment, the trypsin may be a type of bovine pancreases trypsin, a type of porcine pancreases trypsin, or a human trypsin.

In certain embodiments, after the step of performing proteolysis of the first solution using the second protease to obtain the second solution, and before the step of purifying the collagen active peptides from the second solution: the method further include deactivate the enzymolysis of the first and the second enzymes. For example, by adjusting the pH of the second solution to pH5.5-6.5, the papain and the trypsin in the second solution may be deactivated. After that, the second solution with enzymes deactivated is cooled to be below 40° C. to obtain a crude product solution.

Then the collagen active peptides contained in the crude production solution are purified. In certain embodiments, several filtering processes are performed to the crude production solution. In certain embodiments, a first filtering is performed to the crude product solution using a cotton cake filter to obtained a filtered crude product solution. Then a second filtering is performed to the filtered crude product solution using an ultrafiltration membrane having a molecular weight cutoff of 1500 Da to obtain a first filtrate. After that, a third filtering is performed to the first filtrate with an ultrafiltration membrane having a molecular weight cutoff of 300 Da to obtain a concentrated solution. The concentrated solution may be lyophilized to obtain a lyophilized product. The lyophilized product can be further purified using cation exchange chromatography to obtain a purified product. The purified product may be desalted to obtain a collagen active peptides solution. The collagen active peptides solution can then be lyophilized to obtain the collagen active peptide in a form of powder.

In certain embodiments, during the step of the second filtering, a concentration of the collagen active peptides in the crude product solution is maintained at 5+/−0.5%, and when the concentration of the collagen active peptides in the filtrate is below 0.1%, the second filtering is stopped; and during the step of the third filtering, when the concentration of the collagen active peptides having a molecular weight being lower than 300 Da in the second filtrate is lower than 0.1%, the third filtering is stopped.

Example 1: Preparing of Bovine Bone Collagen Active Peptides (1) 2 kg of bovine bone gelatin was weighed, and dissolved in distilled water to obtain a gelatin water solution, where a weight ratio of the gelatin to water is 1:4.

(2) The gelatin water solution was heated to 60° C. The pH of the gelatin water solution was adjusted using 1% sodium bicarbonate water solution to pH6.0. 4 gram (g) of papain was added, and the solution was hydrolyzed for 3 h at 60° C. to obtain a first enzymolysis reaction solution.

(3) The pH of the first enzymolysis reaction solution was adjusted to pH8.5 using food grade sodium hydroxide. 4 g of trypsin was added, and the solution was continuously hydrolyzed for 2 h at 55° C. to obtain a second enzymolysis reaction solution.

(4) The pH of the second enzymolysis reaction solution was adjusted to pH6.5 using a food grade citric acid solution to obtain a crude product solution.

(5) The crude product solution was heated to 95° C. and maintained for 15 min to deactivate the papain and the trypsin. Then the crude product solution was cooled to 40° C. within 30 min using a cooling circulating system.

(6) The crude product solution was filtered with a cotton cake filter to remove naked-eye visible impurities in the solution.

(7) The crude product solution filtered in step (6) was further filtered using an ultrafiltration membrane having a molecular weight cutoff of 1500 Da to obtain a first filtrate. The selected membrane is a model 1500 Da ultrafiltration membrane from GE Company. The membrane has a working pressure of 1.2 MPa and a working temperature of 45° C. The concentration of the crude product solution was controlled at 5%. After filtering, the concentration of the collagen active peptides in the crude product solution increased, and the concentration of the collagen active peptides in the crude product solution was maintained at 5%+/−0.5 constantly by adding pure water into the crude product solution. The filtering was stopped after the concentration of the collagen active peptides in the first filtrate is lower than 0.1%, and then all of the first filtrate was collected.

(8) The first filtrate was concentrated using a 300 Da nanofiltration membrane from GE Company to obtain a concentrated solution and a second filtrate. The membrane has a working pressure of 1.2 MPa and a working temperature of below 45° C. When the concentration of the collagen active peptides in the second filtrate was lower than 0.1%, the concentrating was stopped, and the concentrated solution was lyophilized to obtain collagen active peptides powder.

Figure 1:
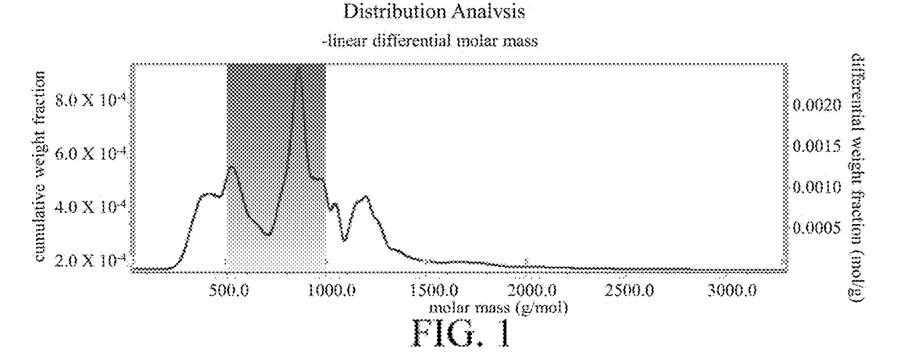
FIG. 1 shows molecular weight distribution analysis of bovine bone collagen active peptides.
Figure 2:
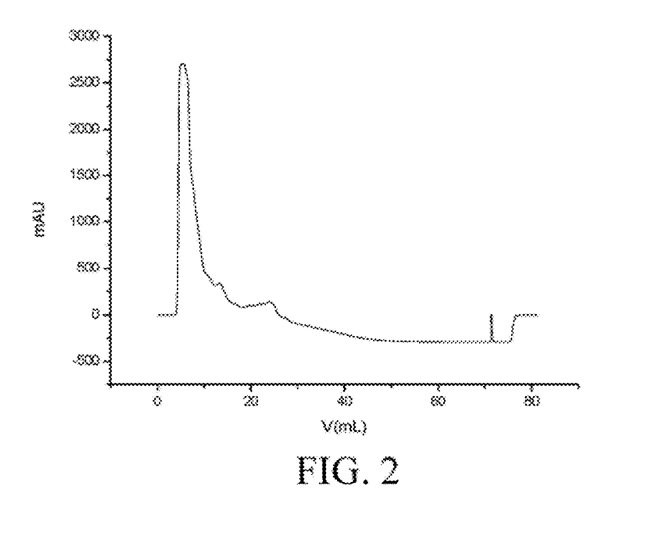
FIG. 2 shows an ion exchange chromatography of low molecular weight collagen active peptides, where mAu represents light absorption value.
Figure 3:
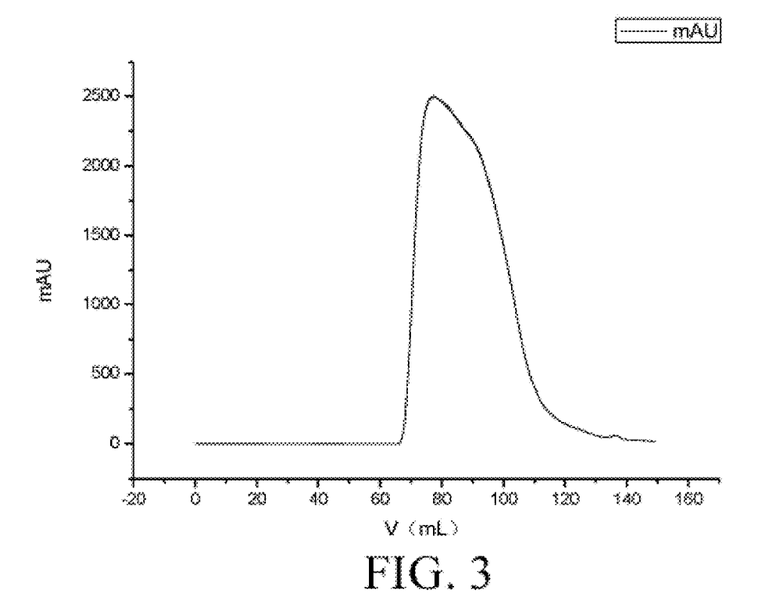
FIG. 3 shows a gel filtration chromatography for desalting low molecular weight collagen active peptides.

(9) The product in step (8) was purified using a cation exchange column with specific steps of: dissolving 30 mg of collagen active peptides powder in 1 mL of initial buffer solution A (50 mM sodium acetate solution, pH5), injecting the obtained solution into a 1 mL sample loop, and separating using a 5 mL Hitrap™$^{SP}$HP prepacked column (GE Company). The specific separating process includes: after balancing 3 column volumes with the initial buffer solution A, loading the sample, washing the column with 2 column volumes (10 mL) of the initial buffer solution A, performing linear gradient elution with 20 column volumes (100 mL) of the eluting buffer solution B (50 mM sodium acetate buffer solution, 2M NaCl, pH5), and balancing the column with 5 column volumes of the initial buffer solution. All the experiment processes were performed on AVANT150, the detection wavelength is 220 nm, the buffer solution flow rate is 1 mL/min, the penetration peak at a retention time $t_R$=7.5 min position was collected, and the chromatogram was as shown in FIG. 2. Then the purified product was dried by vacuum drying.

(10) The purified product in step (9) was desalted using gel filtration column to obtain a collagen active peptides solution. The specific steps include: balancing one column volume with ultrapure water at a flow rate of 1 mL/min, injecting 1 mL of 25 mg/mL of saliferous collagen active peptides into a sample loop, and eluting for 0.8 column volume with ultrapure water at a flow rate of 1 mL/min. All the experiment processes were performed on AVANT150, the detection wavelength was 220 nm, and the peak at a retention time $t_R$=75 min position was collected.

(11) The collagen active peptides solution in step (10) was lyophilized (freezing and drying) to obtain powdery collagen active peptides.

TABLE 1

Molecular weight distribution of bovine bone collagen active peptides.

| Distribution range | Cumulative content (%) | Weight-average molecular weight Mw |
|---|---|---|
| 40.0-500.0 g/mol | 16.3 | 878 (5%) |
| 500.0-1000.0 g/mol | 55.9 | |
| 1000.0-1500.0 g/mol | 22.5 | |
| 1500.0-2000.0 g/mol | 3.5 | |
| 2000.0-3285.0 g/mol | 1.9 | |

Example 2: Antiproliferative Activity Against Ovarian Carcinoma Cell (1) Cell Culture The ovarian carcinoma cells SKOV3, OVCAR3, 436 and SRO82 were cultured on a RPMI 1640 culture medium containing 10% of calf serum and 1% of dual antibiotics (100 U/mL of penicillin and 100 U/mL of streptomycin) in a $CO_2$ incubator having 5% of $CO_2$ and a saturated humidity at 37° C. Cells at logarithmic phase were collected for the following experiment.

(2) Influence of total collagen active peptides in Example 1 on proliferation of SKOV3, OVCAR3, 436 and SRO82 cells by MTT colorimetric method Collagen active peptides were dissolved in the RPMI 1640 culture medium containing 10% of calf serum and 1% of dual antibiotics (100 U/mL of penicillin and 100 U/mL of streptomycin), and then prepared into collagen active peptides solutions with the concentrations of 0.8, 1.6, 3.2, 6.25, 12.5 and 25 mg/mL, which were used for the MTT dosing experiment.

Cells at logarithmic phase were inoculated into a 96 well cell culture plate with $2 \times 10^4$ cells in each well. Each well was added with 100 μL cell suspension. The cells were cultured for 24 h in the cell incubator, and the cell adhering state was checked.

The 96 well cell culture plate with good adhered cells was used for the following dosing experiment. All the culture medium in the wells were pipetted out, and the collagen active peptides solutions of different concentrations of 0.8, 1.6, 3.2, 6.25, 12.5 and 25 mg/mL were respectively added to corresponding wells. A control group was prepared by adding only RPMI 1640 culture medium containing 10% of calf serum and 1% of dual antibiotics (100 U/mL of penicillin and 100 U/mL of streptomycin) without adding the collagen active peptides solutions. 4 same cell wells were prepared for each concentration group. The wells were treated for 120 h. After culturing, 25 μL of 5 mg/mL MTT solution was added into each well, and the plate was placed in the incubator and continued culturing for 4 h. Then 100 μL of 10% SDS-0.1 M HCl solution was added into each well. The plate was placed in the incubator overnight, so as to fully dissolve bluish violet precipitation. The absorbance at 570 nm was measured using a microplate reader.

Figure 4:
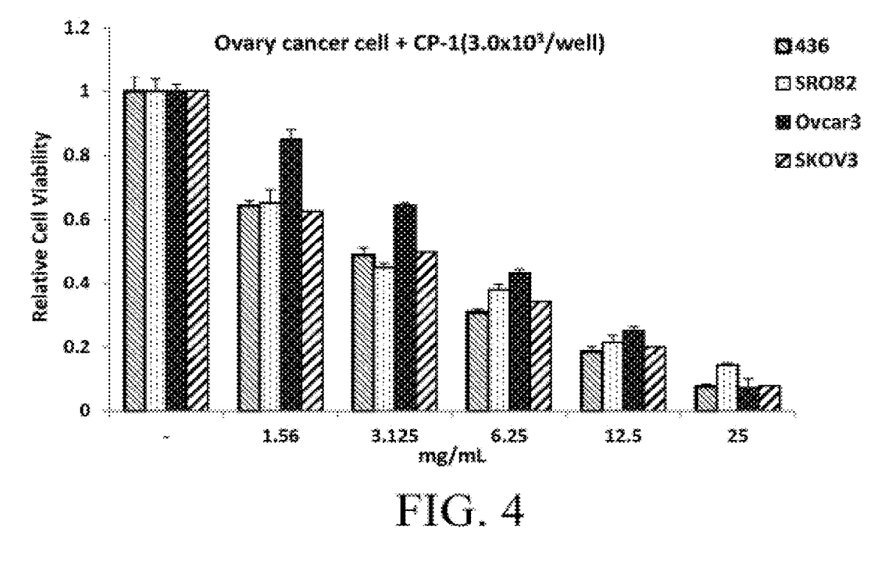
FIG. 4 shows an antiproliferative activity of the bovine bone collagen active peptides against ovarian carcinoma cells by [3-(4,5-dimethylthiazol-2-yl)-2,5-diphenyl-tetrazolium bromide] (MTT).

The antiproliferative activity of the collagen active peptides against the ovarian carcinoma cells SKOV3, OVCAR3, 436 and SRO82 is shown in FIG. 4. The results showed an obvious dose-response relationship, and the $IC_{50}$ were respectively 3.2 mg/mL, 3.7 mg/mL, 3.2 mg/mL and 3.3 mg/mL.

Example 3: Antiproliferative Activity Against Prostate Cancer Cell (1) Cell Culture The prostate cancer cells PC3, LnCAPC1 and LnCAPC2 were cultured on a RPMI 1640 culture medium containing 10% of calf serum and 1% of dual antibiotics (100 U/mL of penicillin and 100 U/mL of streptomycin) in a $CO_2$ incubator having 5% of $CO_2$ and a saturated humidity at 37° C. Cells at logarithmic phase were collected for the following experiment.

(2) Influence of total collagen active peptides in embodiment 1 on proliferation of the prostate cancer cells PC3, LnCAPC1 and LnCAPC2 by an MTT colorimetric method Collagen active peptides were dissolved in the RPMI 1640 culture medium containing 10% of calf serum and 1% of dual antibiotics (100 U/mL of penicillin and 100 U/mL of streptomycin), and then prepared into collagen active peptides solutions with the concentrations of 0.8, 1.6, 3.2, 6.25, 12.5 and 25 mg/mL, which were used for the MTT dosing experiment.

Cells at logarithmic phase were inoculated into a 96 well cell culture plate with $2 \times 10^4$ cells in each well. Each well was added with 100 μL cell suspension. The cells were cultured for 24 h in the cell incubator, and the cell adhering state was checked. The 96 well cell culture plate with good adhered cells was used for the following dosing experiment. All the culture medium in the wells was pipetted out, and the collagen active peptides solutions of different concentrations of 0.8, 1.6, 3.2, 6.25, 12.5 and 25 mg/mL were respectively added to corresponding wells. A control group was prepared by adding only RPMI 1640 culture medium containing 10% of calf serum and 1% of dual antibiotics (100 U/mL of penicillin and 100 U/mL of streptomycin) without adding the collagen active peptides solutions. 4 same cell wells were prepared for each concentration group. The wells were treated for 120 h. After culturing, 25 μL of 5 mg/mL MTT solution was added into each well, and the plate was placed in the incubator and continued culturing for 4 h. Then 100 μL of 10% SDS-0.1 M HCl solution was added into each well. The plate was placed in the incubator overnight, so as to fully dissolve bluish violet precipitation. The absorbance at 570 nm was measured using a microplate reader.

Figure 5:
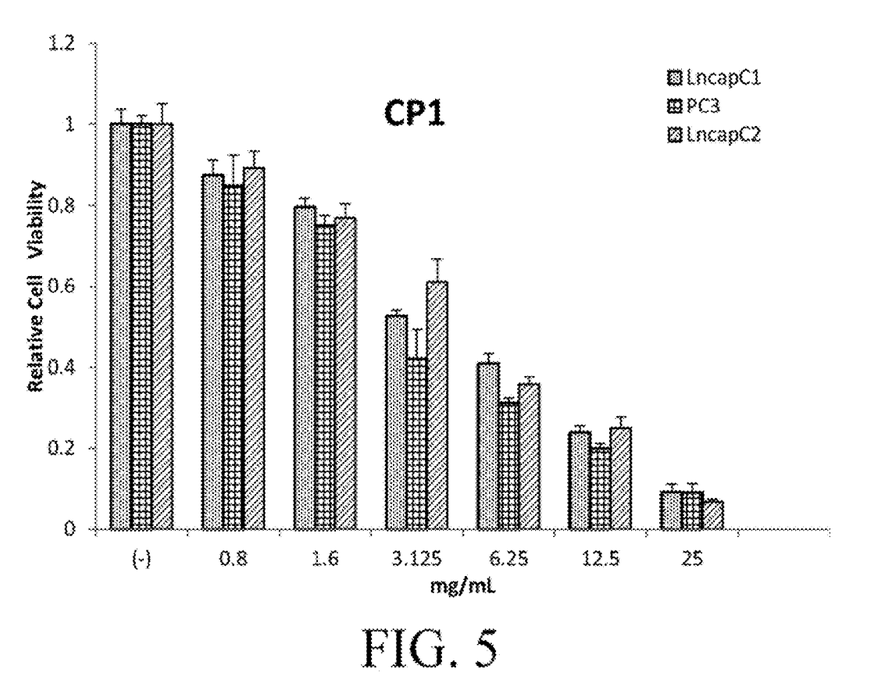
FIG. 5 shows an antiproliferative action of the bovine bone collagen active peptides against prostate cancer cell by MTT.

The biological activity of the collagen active peptides was shown by inhibiting proliferation of the prostate cancer cells PC3, LnCAPC1 and LnCAPC2. The proliferation inhibiting effect of the collagen active peptides on the prostate cancer cells PC3, LnCAPC1 and LnCAPC2 was determined by the MTT method, and was shown in FIG. 5. The results showed that the collagen active peptides can obviously inhibit the proliferation of the prostate cancer cells PC3, LnCAPC1 and LnCAPC2, and has an obvious dose-response relationship, and the IC50 are respectively, 4.1 mg/mL, 4.4 mg/mL and 4.4 mg/mL.

Example 4: Preparation of Porcine Bone Collagen Active Peptides (1) 2 kg of porcine bone gelatin was weighed, and dissolved in distilled water to obtain a gelatin water solution, where a weight ratio of the gelatin to water is 1:10.

(2) The gelatin water solution was heated to 50° C. The pH of the gelatin water solution was adjusted using a 1% sodium bicarbonate water solution to pH6.5. 40 g of papain was added, and the solution was hydrolyzed for 30 min at 50° C. to obtain a first enzymolysis reaction solution.

(3) The pH of the first enzymolysis reaction solution was adjusted to pH8.0 using food grade sodium hydroxide. 40 g trypsin was added, and the solution was continuously hydrolyzed for 30 min at 60° C. to obtain a second enzymolysis reaction solution. The pH was adjusted to pH6.0 using a food grade citric acid solution to obtain a crude product solution.

(4) The crude product solution was heated to 100° C., and maintained for 15 min to deactivate the papain and trypsin. Then the crude product solution was cooled to below 40° C. within 30 min using a cooling circulating system.

(5) Deionized water was added into the crude product solution and the concentration of collagen active peptides in the crude product solution was controlled to be at 5+/−0.5%.

(6) The crude product solution was filtered with a cotton cake filter to remove naked-eye visible impurities in the solution.

(7) the crude product solution filtered in step (6) was further filtered using an ultrafiltration membrane having a molecular weight cutoff of 1500 Da to obtain a first filtrate. The selected membrane is a model 1500 Da ultrafiltration membrane from GE Company. The membrane has a working pressure of 1.2 MPa and a working temperature of below 45° C. The concentration of the crude product solution was controlled to be at 5%. After filtering, the concentration of the crude product solution increased, and the concentration of collagen active peptides in the crude product solution was maintained at 5%+/−0.5 constantly by adding pure water into the crude product solution. The filtering was stopped after the concentration of the collagen active peptides in the first filtrate was lower than 0.1%, and then all of the first filtrate was collected.

(8) The first filtrate was further concentrated using a 300 Da nanofiltration membrane from GE Company to obtain a concentrated solution and a second filtrate. The membrane has a working pressure of 1.2 MPa and a working temperature of below 45° C. When the concentration of the collagen active peptides in the second filtrate was lower than 0.1%, the concentrating was stopped, and the concentrated solution was lyophilized.

(9) The product in step (8) was purified using a cation exchange column with specific steps of: dissolving 30 mg of collagen active peptides powder in 1 mL of initial buffer solution A (50 mM sodium acetate solution, pH5), injecting the obtained solution into a 1 mL sample loop, and separating using a 5 mL Hitrap™ HP prepacked column (GE Company). The specific separating process includes: after balancing 3 column volumes (15 mL) with the initial buffer solution A, loading the sample, washing the column with 2 column volumes (10 mL) of the initial buffer solution A, performing linear gradient elution with 20 column volumes (100 mL) of the elution buffer solution B (50 mM sodium acetate buffer solution, 2M NaCl, pH5), and balancing the column with 5 column volumes of the initial buffer solution. All the experiment processes were performed on AVANT150, the detection wavelength was 220 nm, the buffer solution flow rate is 1 mL/min, the penetration peak at a retention time $t_R$=7.5 min position was collected. Then the purified product was dried by vacuum drying.

(10) The purified product in step (9) was desalted using gel filtration column to obtain a collagen active peptides solution. The specific steps include: balancing one column volume with ultrapure water at a flow rate of 1 mL/min, injecting 1 mL of 25 mg/mL of saliferous collagen active peptides into a sample loop, and eluting for 0.8 column volume with ultrapure water at a flow rate of 1 mL/min. All the experiment processes were performed on AVANT150, the detection wavelength was 220 nm, and a peak at a retention time $t_R$=75 min position was collected.

(11) The collagen active peptides solution in step (10) was lyophilized to obtain powdery collagen active peptides.

The antiproliferative activity against cancer cells of the obtained collagen active peptides was detected according to the methods of embodiments 2 and 3, and the result is similar to those of the embodiments 2 and 3.

Example 5: Preparing of Bovine Bone Collagen Active Peptides (1) 2 kg of bovine bone gelatin was weighed, and dissolved in distilled water to obtain a gelatin water solution, where a weight ratio of the gelatin to water is 1:4.

(2) The gelatin water solution was heated to 75° C. The pH of the gelatin water solution was adjusted using a 1% citric acid water solution to pH5.0. 10 g of papain was added, and the solution was hydrolyzed for 1.5 h at 45° C. to obtain a first enzymolysis reaction solution.

(3) The pH of the first enzymolysis reaction solution was adjusted to pH8.5 using food grade sodium hydroxide. 10 g of trypsin was added, and the solution was continuously hydrolyzed for 1.5 h at 50° C. to obtain a second enzymolysis reaction solution. The pH of the second enzymolysis reaction solution was adjusted to pH6.5 using a food grade citric acid solution to obtain a crude product solution.

(4) The second enzymolysis reaction solution was heated to 95° C., and maintained for 15 min to deactivate the protease. Then the crude product solution was cooled to below 40° C. within 30 min using a cooling circulating system.

(5) Deionized water was added into the crude product solution and the concentration of the collagen active peptides in the crude product solution was controlled to be at 5%.

(6) The crude product solution was filtered with a cotton cake filter to remove naked-eye visible impurities in the solution.

(7) The crude product solution filtered in step (6) was further filtered using an ultrafiltration membrane having a molecular weight cutoff of 1500 Da to obtain a first filtrate. The selected ultrafiltration membrane is a 1500 Da ultrafiltration membrane from GE Company. The membrane has a working pressure of 1.2 MPa and a working temperature of below 45° C. The concentration of the active peptides in the crude product solution was controlled at 5%. After filtering, the concentration of the collagen active peptides in the crude product solution increased, the concentration of collagen active peptides in the crude product solution was maintained at 5%+/−0.5 constantly by adding pure water into the crude product solution. The filtering was stopped after the concentration of collagen active peptides in the first filtrate was lower than 0.1%, and then all of the first filtrate was collected.

(8) The first filtrate was further concentrated using a 300 Da nanofiltration membrane from GE Company to obtain a concentrated solution and a second filtrate. The membrane has working pressure of 1.2 MPa and a working temperature of below 45° C. When the concentration of the collagen active peptides in the second filtrate was lower than 0.1%, the concentrating was stopped, and the concentrated solution was lyophilized to obtain collagen active peptides power.

(9) The product in step (8) was further purified using a cation exchange column with specific steps of: dissolving 30 mg of collagen active peptides powder in 1 mL of initial buffer solution A (50 mM sodium acetate solution, pH5), injecting the obtained solution into a 1 mL sample loop, and separating using a 5 mL Hitrap™ HP prepacked column (GE Company). The specific separating process includes: after balancing 3 column volumes with the initial buffer solution A, loading the sample, washing the column with 2 column volumes (10 mL) of the initial buffer solution A, performing linear gradient eluting with 20 column volumes (100 mL) of the eluting buffer solution B (50 mM sodium acetate buffer solution plus 2M NaCl, pH5), balancing the column with 5 column volumes of the initial buffer solution. All the experiment processes were performed on AVANT150, the detection wavelength was 220 nm, the buffer solution flow rate is 1 mL/min, the penetration peak at a retention time $t_R$=7.5 min position was collected. Then the purified product was dried by vacuum drying.

(10) The purified product in step (9) was desalted using gel filtration column to obtain a collagen active peptides solution. The specific steps includes: balancing one column volume with ultrapure water at a flow rate of 1 mL/min, injecting 1 mL of 25 mg/mL of saliferous collagen active peptides into a sample loop, and eluting for 0.8 column volume with ultrapure water at a flow rate of 1 mL/min. All the experiment processes were performed on AVANT150, the detection wavelength was 220 nm, and the peak at a retention time $t_R$=75 min position was collected.

(11) The collagen active peptides solution in step (10) was lyophilized to obtain powdery collagen active peptides.

The antiproliferative activity of the obtained collagen active peptides against cancer cell was detected according to the methods of embodiments 2 and 3, and the result is similar to those of the embodiments 2 and 3.

The foregoing description of the exemplary embodiments of the present disclosure has been presented only for the purposes of illustration and description and is not intended to be exhaustive or to limit the present disclosure to the precise forms disclosed. Many modifications and variations are possible in light of the above teaching.

The embodiments are chosen and described in order to explain the principles of the present disclosure and their practical application so as to activate others skilled in the art to utilize the present disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A method of preparing collagen active peptides with antiproliferative activity against cancer cells, the method comprising:
   (1) mixing gelatin with water to form a 10-25% gelatin solution;
   (2) heating the gelatin solution to 40-75° C., adjusting a pH of the gelatin solution to pH_5.0-6.5, and adding papain for enzymolysis to obtain a first enzymolysis reaction solution;
   (3) adjusting a temperature of the first enzymolysis reaction solution to 40-75° C., adjusting a pH of the first enzymolysis reaction solution to pH_7.0-8.5, and adding trypsin to obtain a second enzymolysis reaction solution;
   (4) adjusting a pH of the second enzymolysis reaction solution to pH_5.5-6.5;
   (5) deactivating the papain and the trypsin in the second enzymolysis reaction solution, and then cooling the second enzymolysis reaction solution to be below 40° C. to obtain a crude product solution;
   (6) filtering the crude product solution to obtained a filtered crude product solution;
   (7) filtering the filtered crude product solution using an ultrafiltration membrane having a molecular weight cutoff of 1500 Da to obtain a first filtrate;
   (8) filtering the first filtrate with an ultrafiltration membrane having a molecular weight cutoff of 300 Da to obtain a concentrated solution, and lyophilizing the concentrated solution to obtain a lyophilized product;
   (9) purifying the lyophilized product obtained in step (8) using a cation exchange column to obtain a purified product;
   (10) desalting the purified product in step (9) to obtain a collagen active peptides solution; and
   (11) lyophilizing the collagen active peptides solution in step (10) to obtain powdery collagen active peptides, wherein the collagen active peptides have antiproliferative activity against cancer cells.

2. The method of claim 1, wherein an enzyme dosage of the papain is 1%0-2% of a dry mass of the gelatin, and a total enzymolysis reaction time by the papain is 30 min-4 h.

3. The method of claim 1, wherein an enzyme dosage of trypsin is 1%0-2% of dry mass of the gelatin, and enzymolysis reaction time by the trypsin is 30 min-4 h.

4. The method of claim 1, wherein the gelatin is selected from one or more of bovine bone gelatin, pig bone gelatin and fish skin gelatin.

5. The method of claim 1, wherein the second enzymolysis action solution in step (5) is cooled by a cooling circulating system.

6. The method of claim 1, wherein a pH value of the first enzymolysis solution in step (3) is adjusted using sodium hydroxide, sodium bicarbonate or potassium citrate; and a pH value of the second enzymolysis solution in step (4) is regulated by citric acid, acetic acid or phosphoric acid.

7. The method of claim 6, wherein the sodium hydroxide is a food grade sodium hydroxide, the citric acid is a food grade citric acid.

8. The method of claim 1, wherein a pH value of the gelatin solution in step (2) is adjusted using sodium bicarbonate, phosphoric acid or citric acid.

9. The method of claim 1, wherein the crude product solution is filtered by a cotton cake filter.

10. The method of claim 1, wherein during the filtering of step (7), a concentration of the collagen active peptides in the crude product solution is maintained at 5+/−0.5%, and when the concentration of the collagen active peptides in the filtrate is below 0.1%, the filtering is stopped.

11. The method of claim 1, wherein in step (8), when the concentration of the collagen active peptides having a molecular weight being lower than 300 Da in the second filtrate is lower than 0.1%, the concentrating is stopped.

12. A method of preparing collagen active peptides with antiproliferative activity against cancer cells, the method comprising:
   performing proteolysis of gelatin using a first protease to obtain a first solution;
   performing proteolysis of the first solution using a second protease to obtain a second solution; and
   purifying collagen active peptides from the second solution, said purifying comprising:
      performing a first filtering of a crude product solution using a cotton cake filter to obtained a filtered crude product solution;
      performing a second filtering of the filtered crude product solution using an ultrafiltration membrane having a molecular weight cutoff of 1500 Da to obtain a first filtrate;
      performing a third filtering of the first filtrate with an ultrafiltration membrane having a molecular weight cutoff of 300 Da to obtain a concentrated solution, and lyophilizing the concentrated solution to obtain a lyophilized product;
      performing cation exchange chromatography of the lyophilized product to obtain a purified product;
      desalting the purified product to obtain a collagen active peptides solution; and
      lyophilizing the collagen active peptides solution to obtain the collagen active peptides in a form of powder, wherein the collagen active peptides have antiproliferative activity against cancer cells.

13. The method of claim 12, wherein the gelatin is selected from one or more of bovine bone gelatin, pig bone gelatin and fish skin gelatin.

14. The method of claim 12, wherein the first protease is papain, and the step of performing proteolysis of gelatin using the first protease to obtain the first solution comprises:
   mixing the gelatin with water to form a 10-25% gelatin solution; and
   heating the gelatin solution to 40-75° C., adjusting a pH of the gelatin solution to pH_5.0-6.5, and adding the papain for enzymolysis to obtain the first solution.

15. The method of claim 14, wherein an enzyme dosage of the papain is 1‰-2% of a dry mass of the gelatin, and a enzymolysis reaction time by the papain is in a range of about 30 minutes to about 4 hours.

16. The method of claim 12, wherein the second protease is trypsin, and the step of performing proteolysis of the first solution using the second protease to obtain the second solution comprises:
   adjusting a temperature of the first solution to 40-75° C., adjusting a pH of the first solution to pH_7.0-8.5, and adding trypsin to obtain the second solution.

17. The method of claim 16, wherein an enzyme dosage of the trypsin is 1‰-2% of dry mass of the gelatin, and a enzymolysis reaction time by the trypsin is in a range of about 30 minutes to about 4 hours.

18. The method of claim 12, further comprising, after the step of performing proteolysis of the first solution using the second protease to obtain the second solution, and before the step of purifying the collagen active peptides from the second solution, wherein the first protease is papain and the second protease is trypsin:
   adjusting a pH of the second solution to pH_5.5-6.5 to deactivate the papain and the trypsin in the second solution; and
   cooling the second solution to be below 40° C. to obtain the crude product solution.

19. The method of claim 12, wherein
   during the step of the second filtering, a concentration of the collagen active peptides in the crude product solution is maintained at 5+/−0.5%, and when the concentration of the collagen active peptides in the filtrate is below 0.1%, the second filtering is stopped; and
   during the step of the third filtering, when the concentration of the collagen active peptides having a molecular weight being lower than 300 Da in the second filtrate is lower than 0.1%, the third filtering is stopped.

* * * * *